United States Patent [19]
Nakano

[11] Patent Number: 5,402,242
[45] Date of Patent: Mar. 28, 1995

[54] METHOD OF AND AN APPARATUS FOR MEASURING A CONCENTRATION OF A FLUID

[76] Inventor: Yukio Nakano, 1-1-268, Nanryo-cho, Uji-shi, Kyoto 611, Japan

[21] Appl. No.: 147,492

[22] Filed: Nov. 5, 1993

[51] Int. Cl.⁶ .............................................. C01N 21/59
[52] U.S. Cl. ..................................... 356/434; 356/436
[58] Field of Search ......................... 356/433, 434, 436

[56] References Cited
U.S. PATENT DOCUMENTS

| | | | |
|---|---|---|---|
| 3,576,441 | 4/1971 | Adams | 250/564 |
| 3,703,336 | 11/1972 | Rosse et al. | 356/434 |
| 4,566,798 | 1/1986 | Haas | 356/243 |
| 4,737,464 | 4/1988 | McConnell et al. | 436/43 |

*Primary Examiner*—Richard A. Rosenberger
*Attorney, Agent, or Firm*—Oblon, Spivak, McClelland, Maier & Neustadt

[57] ABSTRACT

A method of determining a concentration CM of a component in a sample by measuring a light transmissivity TM of the sample. First, light transmissivities $T_{C1}$ and $T_{C2}$ of a first standard and a second standard respectively having known concentrations C1 and C2 of the component is measured. Then a correction factor K3 is calculated according to the following three equations:

$$L_{C1} = \log((T_{C1} - K3)/(1 - K3)) \quad (1)$$

$$L_{C2} = \log((T_{C2} - K3)/(1 - K3)) \quad (2)$$

$$L_{C1}/L_{C2} = C1/C2 \quad (3)$$

The concentration CM of the sample is calculated according to either of the following equations:

$$CM = ((\log((TM - K3)/(1 - K3))/L_{C1}) \cdot C1 \quad (4)$$

$$CM = ((\log((TM - K3)/(1 - K3))/L_{C2}) \cdot C2 \quad (5)$$

8 Claims, 6 Drawing Sheets

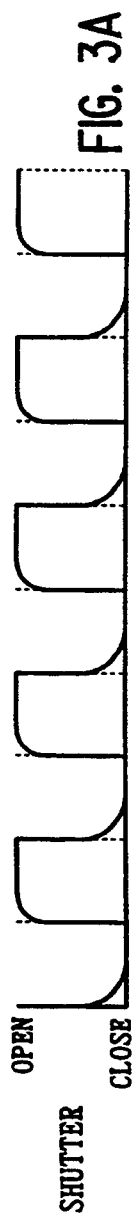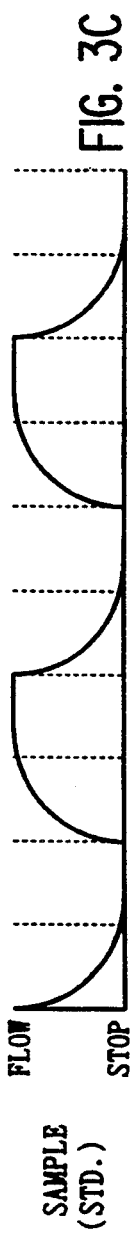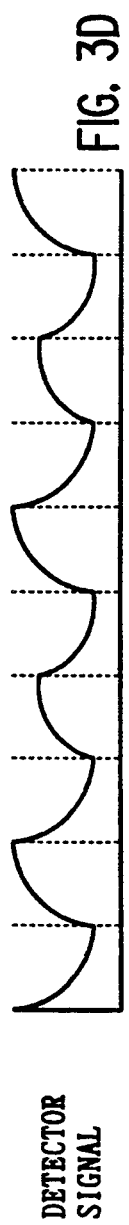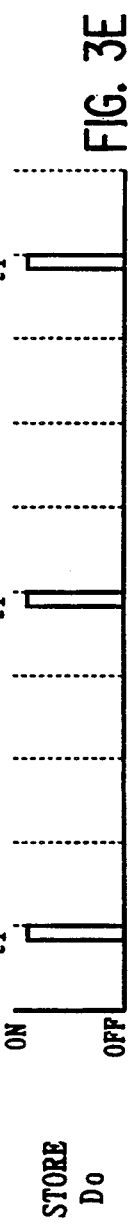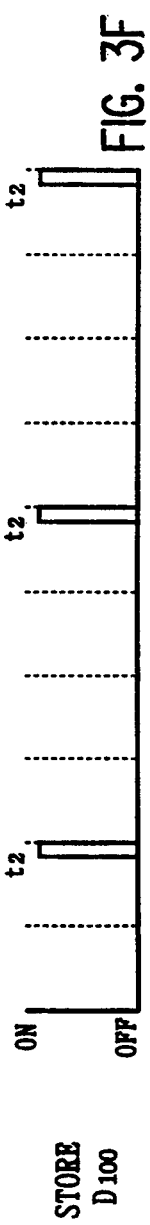

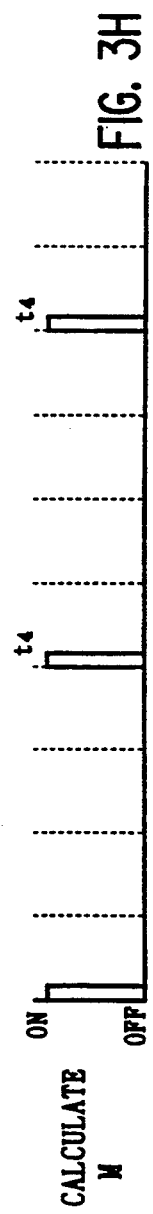
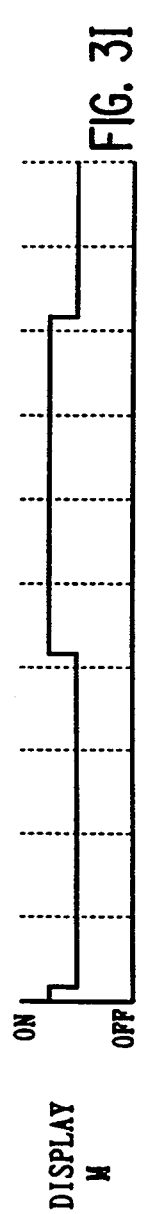
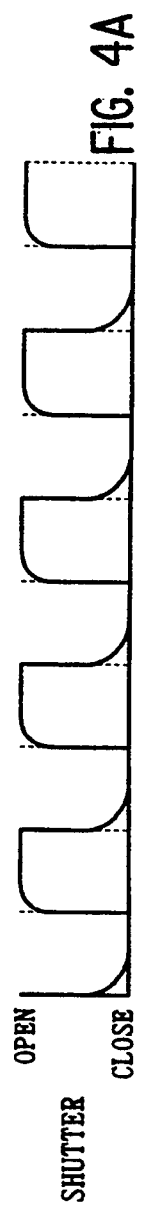
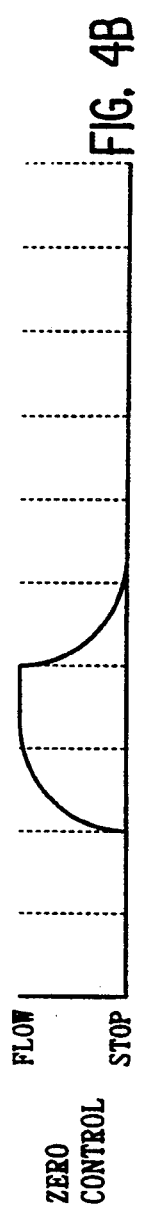
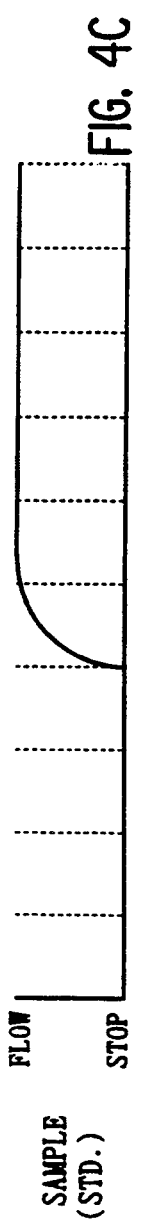
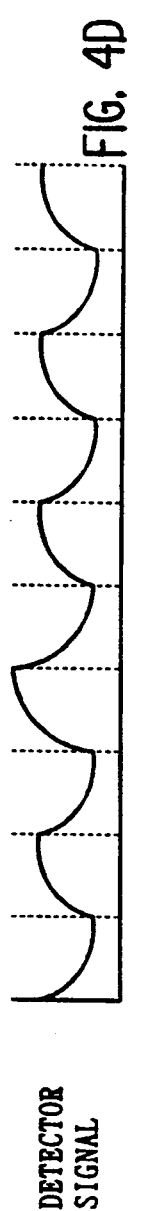
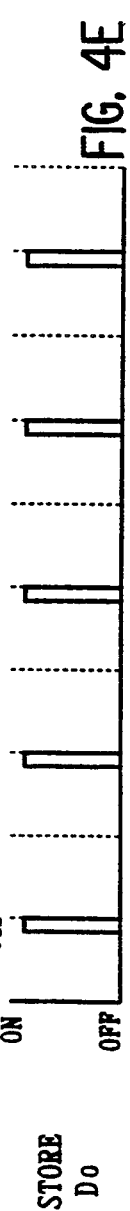

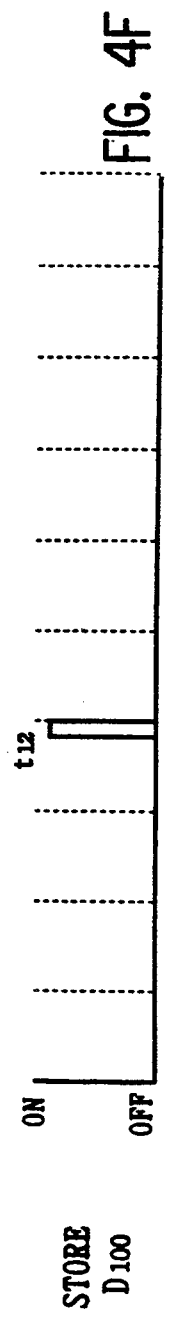
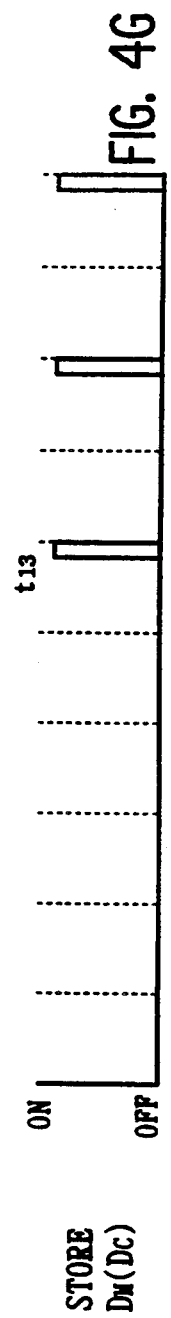
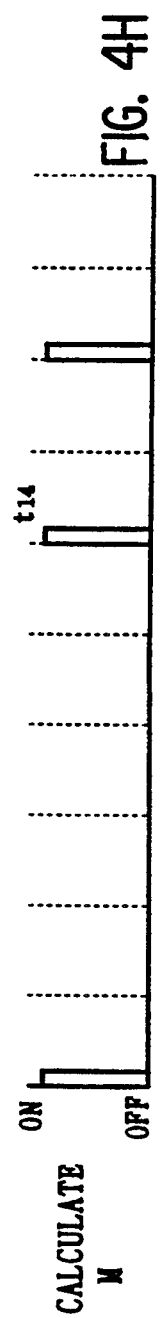
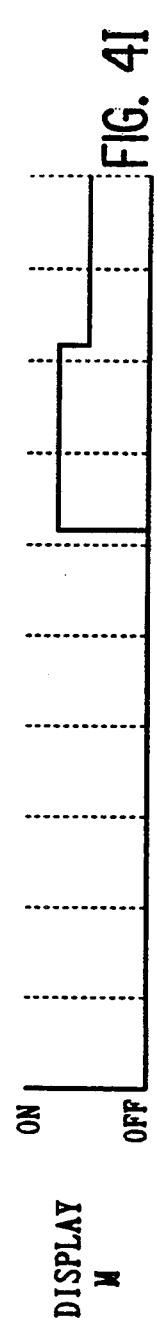

METHOD OF AND AN APPARATUS FOR MEASURING A CONCENTRATION OF A FLUID

BACKGROUND OF THE INVENTION

1. Field of the Invention

The present invention relates to a method of and an apparatus for measuring a concentration of an object component in a fluid (gas or liquid) sample by measuring the absorbed ratio (or transmitted ratio) of light passing through the sample.

2. Description of the Related Art

When, as shown in FIG. 5, an incident light having a strength I0 travels a distance L in a sample gas or liquid containing a component (an object gas or liquid) of concentration C, the strength I of the light becomes, according to the Lambert-Beer's law, $$I = I0 \cdot \exp(-K \cdot C \cdot L) \tag{10}$$

where K is the absorption constant of the component.

The above formula is applicable when the light used is theoretically monochromatic. But when a non-dispersive monochromator such as an optical filter is used to obtain the monochromatic light, which is often the case in normal absorption measuring apparatus, the light is not purely monochromatic. Further, ordinary compact absorption measuring devices are designed to obtain a longer effective traveling distance L of the light so that the light is not parallel in the sample cell but is reflected irregularly by the inner wall of the sample cell. Since, in this case, the traveling distance L of the light passing through the sample is not unique, the Lambert-Beer's law does not apply exactly to actual absorption measuring devices.

Thus conventionally, the data of the light absorption (or transmissivity) of a sample gas is not used by itself but it is compared to that of a reference gas having a known concentration of the object gas. In this case, two absorption (or transmissivity) measurements must be conducted, one for the sample gas and the other for the reference gas. A problem here is that there may arise various differences in the measuring conditions of the two measurements: that is, strength of the source light, light absorbing characteristic of the filters used in the optical paths, quality of the photodetectors and amplifiers, contamination of the sample cells, temperature, pressure, etc. The differences in the measuring conditions cause a zero drift or a span drift in the measured data.

Actually, the calibration curve method is widely used in which a calibration curve (or a working curve) is first established showing a relationship between the concentration and the transmissivity. The calibration curve is made as follows. First a plurality of standard samples are prepared having different known concentrations within a measurement range (for example, 0%, 20%, 40%, 60%, 80%, and 100% of the full scale). Then the light transmissivities of these standard samples are measured, and the measured data is plotted against the known concentration. Since the measured data does not generally constitute a straight line, a linearization device is required for determining corrected scales or performing line approximation. Further, since the characteristics of the calibration curve change according to the aging of each component of the device, regular correction of the calibration curve as of every several (normally one through six) months is thereby recommended (see JIS (Japanese Industrial Standards) K0055 'GENERAL RULES OF GAS ANALYZER CORRECTION', JIS K0115 'GENERAL RULES OF ABSORPTION SPECTROSCOPY', and JIS K0151 'INFRARED GAS ANALYZERS').

SUMMARY OF THE INVENTION

An object of the present invention is therefore to provide an improved method and apparatus for measuring concentration of an object component in a sample gas or liquid which does not require a calibration curve, and still determines the correct concentration of the object component in the sample by correcting a variety of disturbing factors as a whole.

According to the present invention, the method of determining a concentration of a component in a sample includes the following steps:

a) measuring light transmissivities $T_{C1}$ and $T_{C2}$ of a first standard and a second standard respectively having known concentrations C1 and C2 of the component;

b) calculating a correction factor K3 according to the following equations;

$$L_{C1} = \log((T_{C1} - K3)/(1 - K3)) \tag{1}$$

$$L_{C2} = \log((T_{C2} - K3)/(1 - K3)) \tag{2}$$

$$L_{C1}/L_{C2} = C1/C2 \tag{3}$$

c) measuring a light transmissivity TM of the sample having an unknown concentration CM; and d) determining the unknown concentration CM according to either of the following equations.

$$CM = ((\log((TM - K3)/(1 - K3))/L_{C1}) \cdot C1 \tag{4}$$

$$CM = ((\log((TM - K3)/(1 - K3))/L_{C2}) \cdot C2 \tag{5}$$

The equations are introduced as follows. The equation (10) of the Lambert-Beer's Law can be rewritten as $$T = I/I0 = \exp(-K \cdot C \cdot L) \tag{11}$$

which shows that the transmissivity T should converge to zero, as shown in FIG. 6A, when C·L increases (i.e., the concentration C increases or the cell length L increases).

Actually, however, the transmissivity T does not converge to zero but to a certain non-zero value K3, as shown in FIG. 6B, due to various factors as described before. In this case, it is better not to use the value of TM by itself but to use a corrected value $$(TM - K3)/(1 - K3),$$

as shown in FIG. 6B, in calculating the concentration CM from the transmissivity TM. That is, when the transmissivity TM is measured, the original Lambert Beer's Law $$\log(IM/I0) = \log(TM) = -K \cdot CM \cdot L \tag{12}$$

is not used but the formula including the correction factor K3

$$\log((TM - K3)/(1 - K3)) = -K \cdot CM \cdot L \tag{13}$$

is used to calculate the concentration CM.

The correction factor K3 can be obtained as follows. Transmissivities TC1 and TC2 of two samples having known concentrations C1 and C2 are measured, and the values are put into the equation (13) as $$\log((T_{C1}-K3)/(1-K3))=L_{C1} \quad (14);$$

$$\log((T_{C2}-K3)/(1-K3))=L_{C2} \quad (15); \text{ and}$$

$$L_{C1}/L_{C2}=(-K\cdot C1\cdot L)/(-K\cdot C2\cdot L)=C1/C2 \quad (16).$$

The correction factor K3, as well as the two unknowns $L_{C1}$ and $L_{C2}$, can be obtained from the three equations (14) through (16) since the values of the other variables are all known. The equations (14) through (16) are equal to the above equations (1) through (3), and by substituting CM for C1 or C2 in equations (14) through (15), the equation (4) or (5) can be obtained.

Though the equations (1) through (3) are difficult to solve analytically, it can be easily solved by a computer using a known numerical calculation method.

Alternatively, the method of the present invention includes the steps of:

ab) measuring light transmissivities $T_{C1}$, $T_{C2}$ and $T_{C3}$ of a first standard, a second standard and a third standard respectively having known concentrations C1, C2 and C3 of the component;

bb) calculating a correction factor K3b, K4 and K5 according to the following equations;

$$C2/C1=(((1-T_{C2})/(1-T_{C1}))^{K3b})\cdot K4+((1-T_{C2})/(1-T_{C1}))\cdot K5 \quad (1b)$$

$$C3/C1=(((1-T_{C3})/(1-T_{C1}))^{K3b})\cdot K4+((1-T_{C3})/(1-T_{C1}))\cdot K5 \quad (2b)$$

$$K4-K5=1 \quad (3b)$$

cb) measuring a light transmissivity TM of the sample having an unknown concentration CM; and db) determining the unknown concentration CM according to the following equation.

$$CM=((((1-TM)/(1-T_{C1}))^{K3b})\cdot K4+((1-TM)/(1-T_{C1}))\cdot K5)\cdot C1 \quad (4b)$$

The ratio CM/C1 of an unknown concentration CM to a known concentration C1 and the ratio of corresponding transmissivities $(1-TM)/(1-T_{C1})$ has the relationship as shown in FIG. 7, which can be formulated as:

$$CM/C1=(((1-TM)/(1-T_{C1}))^{K3b})\cdot K4+((1-TM)/(1-T_{C1}))\cdot K5 \quad (13b),$$

which leads to the above equation (4b).

The three unknown factors K3b, K4 and K5 in the above equation (13b) can be calculated by establishing three equations $$C2/C1=(((1-T_{C2})/(1-T_{C1}))^{K3b})\cdot K4+((1-T_{C2})/(1-T_{C1}))\cdot K5 \quad (14b)$$

$$C3/C1=(((1-T_{C3})/(1-T_{C1}))^{K3b})\cdot K4+((1-T_{C3})/(1-T_{C1}))\cdot K5 \quad (15b)$$

$$K4+K5=1 \quad (16b)$$

with CM in equation (13b) substituted by C2 and C3, and TM by $T_{C2}$ and $T_{C3}$ of further two samples having known concentrations. The equations (14b) through (16b) are just the equation (1b) through (3b) and the equation (4b) is obtained by substituting CM for C1 or C2 in equations (14b) through (16b).

Though it is difficult to solve the equations (1b) through (3b) analytically, it is rather easy to obtain the values of K3b, K4 and K5 through a numerical method using a computer. For example, first, the value of K4 is fixed at 1 (K4=1, and K5=0 due to equation (3b)), and the value of K3b is increased from 1 while the right hand side of equation (1b) is calculated repeatedly. When the value comes closer to the value of C2/C1 (left hand side of equation (1b)) than a predetermined difference, the calculation of equation (1b) is stopped. The value of K3b at this time is then put into equation (2b), and the value of K4 is decreased from 1 (so the value of K5 is increased from 0 due to equation (3b)) while the right hand side of equation (2b) is calculated repeatedly. When the value comes closer to the value of C3/C1 (left hand side of equation (2b)) than a predetermined difference, the calculation of equation (2b) is stopped. The values of K4 and K5 at this time are then again put into equation (1b) and the calculation of equation (1b) is repeated varying the value of K3b until the difference becomes less than the predetermined value. Thus repeating the calculation of equations (1b) and (2b), K3b, K4 and K5 converge to a certain values, which are the numerical solution of the equations (1b) through (3b).

When the apparatus used remains the same and the objects of the measurement are similar, the value of K3b can be kept unchanged practically. Thus, in this case, only the other two correction factors K4 and K5 need be modified using two samples of known concentrations. Similarly, it is possible to modify only the value of K3b while the values of K4 and K5 are kept unchanged.

Since there may arise a zero drift or a span drift in the output of a measurement apparatus, the light transmissivity $TA=T_{C1}$, $T_{C2}$, $T_{C3}$ or TM of the first standard, the second standard, the third standard (in case of the latter method) or the sample is preferred to be determined by the following steps introducing a correction factor K1:

e) obtaining a first output DO of a photodetector when no light enters the photodetector, and a second output D100 of the photodetector when light passing through a zero control containing zero percentage of the component enters the photodetector;

f) calculating a correction factor K1 based on the first output DO and the second output D100 as $$K1=1/(D100-D0) \quad (6)$$

and g) measuring an output DA of the photodetector when light passing through the first standard, the second standard, the third standard (in case of the latter method) or the sample enters the photodetector, and determining the transmissivity TA of the first standard, the second standard, the third standard or the sample as $$TA=(DA-D0)\cdot K1 \quad (8).$$

The apparatus for performing the method is described in the following description of the embodiment, and other objects, features, aspects, and advantages of the present invention will also become apparent from the following detailed description of the preferred embodiment with the accompanying drawings.

BRIEF DESCRIPTION OF THE DRAWINGS

FIG. 3 is a timing chart of an automatic successive concentration measurement by the concentration measurement apparatus of the embodiment.

FIG. 4 is a timing chart of a manual concentration measurement.

DETAILED DESCRIPTION OF A PREFERRED EMBODIMENT

Figure 1:
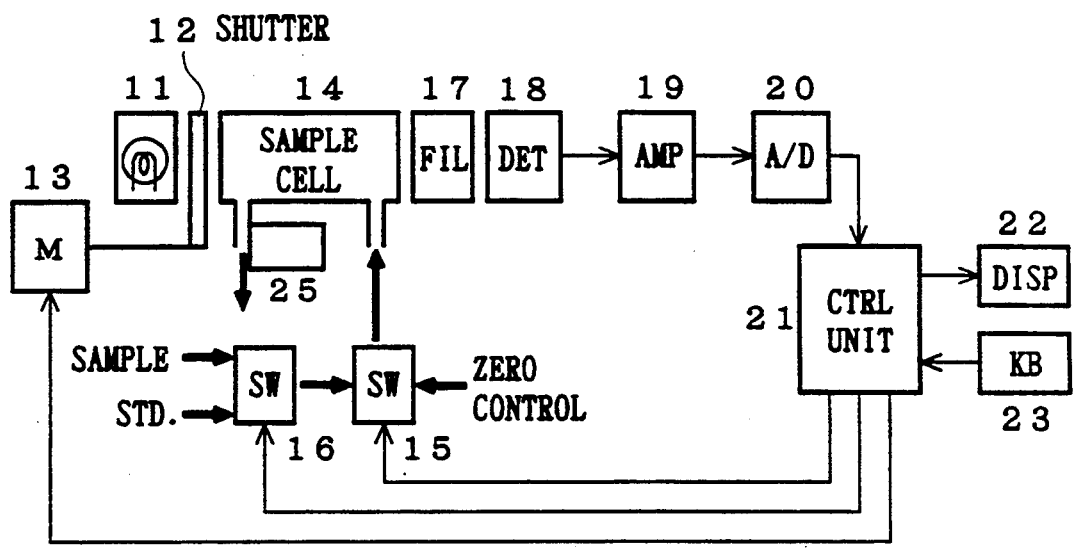
FIG. 1 is a block diagram showing a structure of a concentration measurement apparatus embodying the present invention.
Figure 2:
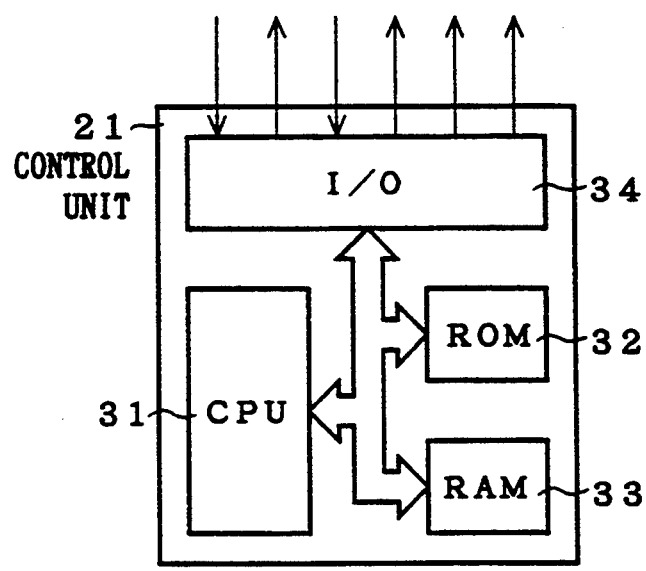
FIG. 2 is a block diagram illustrating a structure of a control unit of the concentration measurement apparatus of the embodiment.
Figure 5:
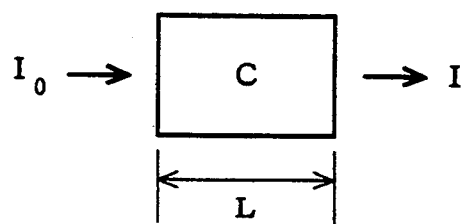
FIG. 5 is an illustration of the Lambert-Beer's law.
Figure 6A:
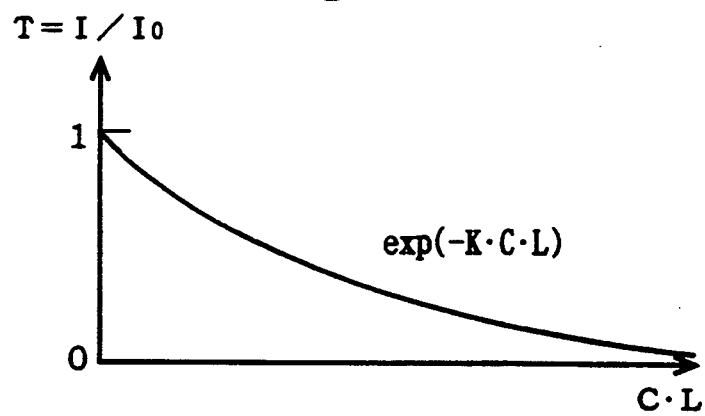
FIG. 6A is a graph of transmissivity according to the Lambert-Beer's law and FIG. 6B is a graph of transmissivity in actual measurement.
Figure 6B:
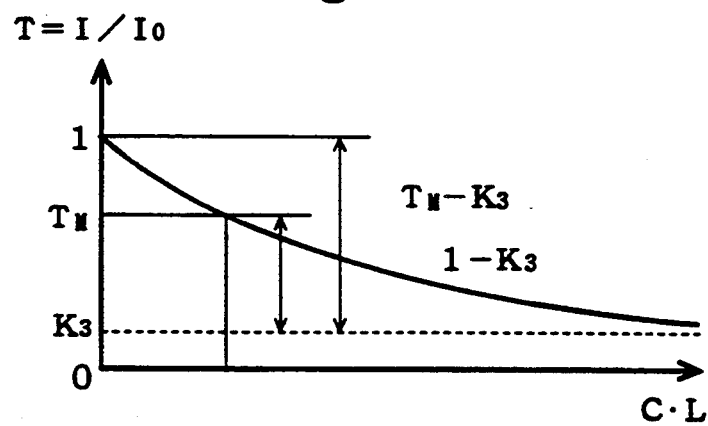
Figure 7:
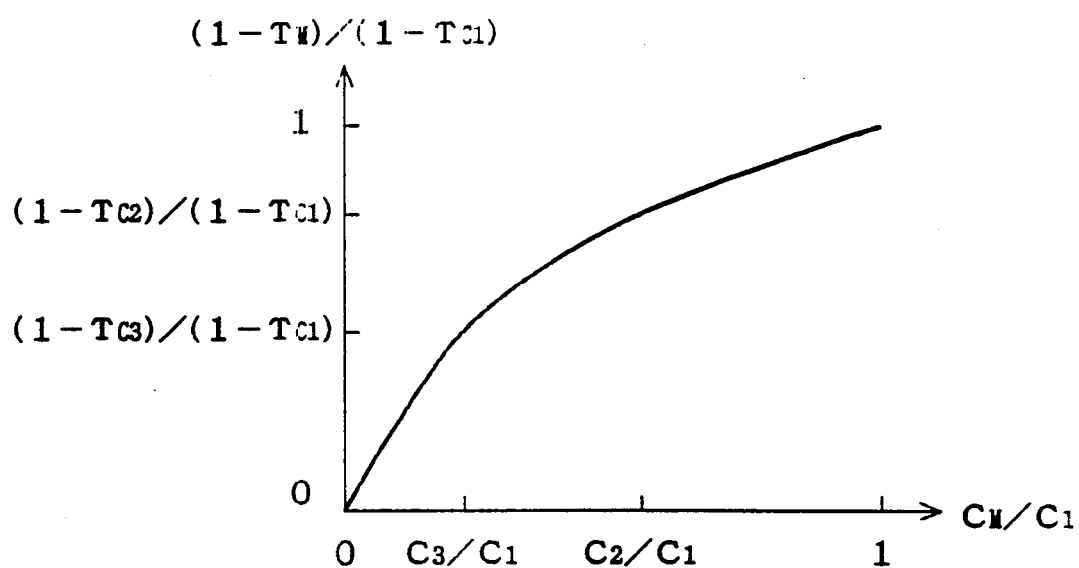
FIG. 7 is a graph showing the relationship between the ratio of transmissivities and the ratio of concentrations.

A concentration measurement apparatus embodying the present invention is described referring to FIGS. 1 through 3. As shown in FIG. 1, light emitted from a direct-current (DC) light source 11 is blocked or allowed passing by a shutter 12 to a sample cell 14. The chopping frequency of the shutter 12 depends on the object of the measurement, but is generally in a range from 1 to 3,600 cycles per minute (0.017 to 60 Hz). The shutter 12 is unnecessary when the light source 11 is controlled by synchronizing pulses. Light allowed by the shutter 12 then passes through the sample cell 14. In the sample cell 14, a zero-concentration fluid (zero control) and a sample fluid (gas or liquid) or a standard fluid are alternately introduced by a first and a second fluid switchers 15 and 16. In an automated concentration measurement, the switching frequency is set no less than twice the chopping frequency of the shutter 12 (or no greater than one half the chopping frequency). The switching frequency also depends on the object, but is generally within a range from 0.1 to 1,200 cpm (0.0017 to 20 Hz). If the concentration measurement apparatus is rather stable, the interval of the introduction of the zero control can be elongated to, say, once a day.

Light passing through the fluid in the sample cell 14 then enters an optical filter (FIL) 17 which removes interfering components from the light, and the light is measured by a photodetector (DET) 18. A signal output from the photodetector 18 representing the quantity of the transmitted light is amplified by an amplifier (AMP) 19 and is given to a control unit 21 via an A/D converter 20.

As shown in FIG. 2, the control unit 21 is essentially composed of a micro-computer including a CPU 31, a ROM 32, a RAM 33, and an I/O interface 34. The CPU 31 controls operation of the components of the concentration measurement apparatus according to programs stored in the ROM 32. The control unit 21 calculates the concentration of the object component in the sample based on the data of the transmitted light quantity detected by the photodetector 18 as described later, and outputs the results on a digital display (DISP) 22. Instructions given by an operator through a keyboard (KB) 23 are also given to the control unit 21.

In the concentration measurement apparatus of the present embodiment, correction process is first executed with the zero control (fluid containing no object component) and two standard fluids each having a known concentration of the object component. The correction process is described referring to the timing chart of FIG. 3.

(A1) The shutter 12 is closed and the zero control is introduced into the sample cell 14. At a first time point t1 which is a predetermined time period after the introduction of the zero control, an output D0 (0% light transmission detection signal) of the photodetector 18 is stored in the RAM 33. The time period is predetermined regarding the stabilizing time of the output from the photodetector 18.

(A2) The shutter 12 is opened (with the zero control remaining in the sample cell 14). At a second time point t2 which is another predetermined time period after the opening of the shutter 12, an output D100 (100% light transmission detection signal) of the photodetector 18 is stored in the RAM 33.

(A3) If necessary, the above steps (A1) and (A2) are repeated, and the mean value of the outputs D0 and the mean value of the outputs D100 are stored in the RAM 33.

(A4) A correction factor K1 is calculated as follows in order to convert the 0% light transmission detection signal D0 and the 100% light transmission detection signal D100 from the photodetector 18 to the proper transmissivity values 0 and 100:

$$K1 = 1/(D100 - D0) \qquad (21).$$

The calculated correction factor K1 is stored in the RAM 33.

(A5) The shutter 12 is closed, and a first standard having a known concentration C1 preferably near the full scale is introduced into the sample cell 14. When the sample cell 14 is filled with the first standard, the shutter 12 is opened. At a third time point t3 which is still another predetermined time period after the shutter 12 is opened, an output $D_{C1}$ of the photodetector 18 is stored in the RAM 33. This measurement may also be repeated a plurality of times to store the mean value of the output $D_{C1}$ in the RAM 33.

(A6) The transmissivity $T_{C1}$ of the first standard (having the known concentration C1) is calculated from the output $D_{C1}$ of the photodetector 18 using the correction factor K1 retrieved from the RAM 33, as:

$$T_{C1} = (D_{C1} - D0) \cdot K1 \qquad (23).$$

(A7) A second standard having another known concentration C2 is introduced into the sample cell 14, and the transmissivity $T_{C2}$ of the second standard is calculated based on an output $D_{C2}$ of the photodetector 18 in the same manner as above:

$$T_{C2} = (D_{C2} - D0) \cdot K1 \qquad (24).$$

(A8) A correction factor K3 is then calculated from the following three equations:

$$L_{C1} = \log((T_{C1} - K3)/(1 - K3)) \qquad (25);$$

$$L_{C2} = \log((T_{C2} - K3)/(1 - K3)) \qquad (26); \text{ and}$$

$$L_{C1}/L_{C2} = C1/C2 \qquad (27).$$

The correction factor K3 can be easily calculated from the equations (25) through (27) by a computer using a known numerical calculation method. For example, a provisional value is substituted into K3, and $L_{C1}$, $L_{C2}$ and $L_{C1}/L_{C2}$ are calculated according to equations (25) through (27). While the provisional value of K3 is gradually increased from 0, the values of $L_{C1}$ and $L_{C2}$ are repeatedly calculated until the value of the ratio $L_{C1}/L_{C2}$ becomes sufficiently close to the value C1/C2.

(A8b) Using the equation (25b) below, the value of K3b is calculated while the values of K4 and K5 are kept fixed to a certain value.

$$C2/C1 = (((1 - T_{C2})/(1 - T_{C1}))^{K3b} \cdot K4 + ((1 - T_{C2})/(1 - T_{C1})) \cdot K5 \quad (25b)$$

Or the values of K4 and K5 are calculated while the value K3b is kept fixed to a certain value according to the following equations.

$$C2/C1 = (((1 - T_{C3})/(1 - T_{C1}))^{K3b} \cdot K4 + ((1 - T_{C3})/(1 - T_{C1})) \cdot K5 \quad (25b)$$

$$K4 + K5 = 1 \quad (26b)$$

The value of K3b or the values of K4 and K5 according to equations (25b) and (26b) can be easily calculated by a known numerical method using a computer. For example, a provisional value 1 is put into the variable K3b and the right hand side of the equation (25b) is calculated with certain provisional values of K4 and K5 (e.g., 1 and 0 respectively). Then the calculated value is compared with the left hand side of the equations respectively. If the difference is greater than a predetermined small value, the value of K3b is increased by a small step and the calculation is repeated. Thus the calculations are repeated until the difference becomes less than the predetermined small value, at which time the value of K3b is fixed. If necessary, the calculations are further repeated with the fixed value of K3b to obtain better values of K4 and K5.

The correction factors K3, K3b, K4 and K5 thus calculated are also stored in the RAM 33. This completes the correction process.

The unknown concentration of a sample is then determined according to the process below.

(B1) The shutter 12 is closed, and the zero control is introduced into the sample cell 14. At a first time point t1, which is a predetermined time period after introducing the zero control, a 0% light transmission detection signal D0 output from the photodetector 18 is stored in the RAM 33.

(B2) The shutter 12 is opened with the zero control remaining in the sample cell 14. At a second time point t2 which is another predetermined time period after the opening of the shutter 12, a 100% light transmission detection signal D100 output from the photodetector 18 is also stored in the RAM 33.

(B3) A correction factor K1 is calculated in the same manner as the above correction step (A4) to convert the 0% light transmission detection signal D0 and the 100% light transmission detection signal D100 to the proper transmissivity values 0 and 100:

$$K1 = 1/(D100 - D0) \quad (21).$$

The calculated correction factor K1 is stored in the RAM 33.

(B4) The shutter 12 is closed, and the sample fluid is introduced into the sample cell 14. After a predetermined time period, the shutter 12 is opened. At a third time point t3 which is another predetermined time period after the opening of the shutter 12, the signal DM output from the photodetector 18 is stored in the RAM 33.

(B5) The detection signal DM is corrected, with the correction factor K1, to a transmissivity TM of the sample as follows:

$$TM = (DM - D0) \cdot K1 \quad (28).$$

(B6) The correction factor K3 determined in the correction process is read out of the RAM 33, and the concentration M of the sample is determined according to the equations below at a fourth time point t4:

$$LM = \log((TN - K3)/(1 - K3)) \quad (29); \text{ and}$$

$$M = (LM/L_{C1}) \cdot C1 \quad (30).$$

(B6b) Or the correction factors K3b, K4 and K5 also determined in the correction process are read out of the RAM 33, and the concentration M of the sample is determined according to the equations below at a fourth time point t4:

$$M = ((((1 - TM)/(1 - T_{C1}))^{K3b} \cdot K4 + ((1 - TM)/(1 - T_{C1})) \cdot K5) \cdot C1 \quad (29b)$$

(B7) The concentration M of the sample thus determined is output on the digital display 22.

In the above correction and measurement process, the control unit 21 controls the first and second fluid switchers 15 and 16 to timely introduce the zero control and the first, second and (if applicable) third standards or the sample into the sample cell 14. The control unit 21 also controls a shutter driving motor (M) 13 to open and close the shutter 12. Thus, by previously instructing repeated operation of such control to the control unit 21, an automatic successive measurement of a plurality of samples can be performed.

A manual measurement is performed as shown in FIG. 4. First, no fluid is introduced into the sample cell 14, and the shutter 12 is closed. At a time point t11 which is a predetermined time period after the shutter 12 is closed, the output D0 of the photodetector 18 is stored in the RAM 33. The time period is predetermined to wait for the stabilization of the output of the photodetector 18. Then, zero control is introduced into the sample cell 14 (by the key operation of the operator or by the control of the control unit 21), and the shutter 12 is opened. At a second time point t12 which is another predetermined time period after the shutter 12 is opened, the output D100 is measured. Sample fluid (or standard fluid) is then introduced into the sample cell 14, and after elapse of a predetermined time period, an output DM (or DC) of the photodetector 18 is measured and stored in the RAM 33 at a third time point t13. At a fourth time point t14, the concentration M of the sample is calculated in the same manner as described above using the measured values D0, D100, DM, and DC all stored in the RAM 33. The calculated result is shown on the digital display 22. After that, outputs D0 and DM of the photodetector 18 are alternately detected, and the concentration values are successively calculated and shown on the display 22. Accuracy of the measurement can be further improved by correcting the results with the output D100 for the zero control detected just before reading the final output DM.

When such a high accuracy is not required, the correction factor K3 may be determined beforehand in a preliminary test, and is previously set through key operation.

Concentration data of each sample calculated by the control unit 21 is output to the digital display 22 in the above embodiment. It may also be converted by a D/A converter to send as an analog signal to a recorder. In this case, previous range selection according to the magnitude of data output from the control unit 21 enables a high resolution analog output without troublesome adjustment of the recorder.

A temperature detector 25 and a barometer or a pressure gauge for measuring the pressure in the sample cell 14 may be provided at an outlet of the sample cell 14 as shown in FIG. 1. This allows determination of highly accurate concentrations with temperature and pressure compensation. In this case, the above equation (30) for determining the concentration M of the sample is modified as:

$$M = [(LM/L_{C1}) \cdot C1] \cdot [(273 + ThM)/(273 + ThC1)] \cdot [(PC1/PM) \cdot K6] \quad (30b)$$

or in the case of equation (29b), $$M = ((((1 - TM)/(1 - T_{C1}))^{K3b}) \cdot K4 + ((1 - TM)/(1 - T_{C1})) \cdot K5) \cdot C1 \cdot [(273 + ThM)/(273 + ThC1)] \cdot [(PC1/PM) \cdot K6] \quad (30c)$$

where
ThC1 is the temperature on measurement of the first standard having the known concentration C1;
PC1 is the atmospheric pressure or the fluid pressure on measurement of the first standard of the known concentration C1;
ThM is the temperature on measurement of the sample:
PM is the atmospheric pressure or the fluid pressure on measurement of the sample; and
K6 is set equal to one for atmospheric pressure compensation, and is set depending on the pressure in the sample cell 14 when the pressure is significantly increased or reduced.

As described above, the concentration measurement apparatus of the invention does not need a preparation of a calibration curve which requires a number of standards, but it can easily and accurately determine the concentration of a sample by correcting a variety of factors affecting measurement of the concentration as a whole.

The essential characteristics of the invention may be applicable to a variety of apparatus other than the concentration measurement apparatus of the above embodiment. Some examples are given below.

A. A multi-component concentration meter including a detector with a plurality of filters having different wave length transmission (or absorption) characteristics or alternatively including a plurality of detectors each having specific wave length characteristics that can measure multiple components simultaneously.

B. A multi-component concentration meter as above but further equipped with a function for correcting the effect of those components interfering with the wave length of the sample, whereby the concentration of a sample is more accurately determined.

C. A concentration meter with an alarm function which compares each measurement value with a predetermined alarm threshold value and outputs an alarm signal when the measurement value exceeds the threshold value. The alarm threshold value may be an upper limit, a lower limit, or a range, and may be determined for each component. The alarm concentration meter may also judge the result of each measurement. In a multi-component concentration meter of this type, a leak alarm may be output when a total of all the components is not greater than a predetermined value.

What is claimed is:

1. A method of determining a concentration of a component in a sample by measuring absorbed ratio or transmitting ratio of light passing through the sample, the method comprising the steps of:

a) measuring light transmissivities and $T_{C1}$ and $T_{C2}$ of a first standard and a second standard respectively having known concentrations C1 and C2 of the component;

b) calculating a correction factor K3 according to the following equations;

$$L_{C1} = \log((T_{C1} - K3)/(1 - K3)) \quad (1)$$

$$L_{C2} = \log((T_{C2} - K3)/(1 - K3)) \quad (2)$$

$$L_{C1}/L_{C2} = C1/C2 \quad (3)$$

c) measuring a light transmissivity TM of the sample having an unknown concentration CM; and d) determining the unknown concentration CM according to either of the following equations:

$$CM = ((\log((TM - K3)/(1 - K3))/L_{C1} \cdot C1 \quad (4)$$

$$CM = ((\log((TM - K3)/(1 - K3))/L_{C2} \cdot C1 \quad (5).$$

2. The concentration measuring method according to claim 1, wherein a light transmissivity $TA = T_{C1}$, $T_{C2}$, or TM of the first standard, the second standard or the sample is determined by the steps of:

e) obtaining a first output D0 of a photodetector when no light enters the photodetector, and a second output D100 of the photodetector when light passing through a zero control containing zero percentage of the component enters the photodetector;

f) calculating a correction factor K1 based on the first output DO and the second output D100 as $$K1 = 1/(D100 - D0) \quad (6)$$

g) obtaining an output DA of the photodetector when light passing through the first standard, the second standard or the sample enters the photodetector, and determining the light transmissivity TA of the first standard, the second standard or the sample as $$TA = (DA - D0) \cdot K1 \quad (8).$$

3. A method of determining a concentration of a component in a sample by measuring absorbed ratio or transmitting ratio of light passing through the sample, the method comprising the steps of:

ab) measuring light transmissivities $T_{C1}$, $T_{C2}$ and $T_{C3}$ of a first standard, a second standard and a third standard respectively having known concentrations C1, C2 and C3 of the component;

bb) calculating a correction factor K3b, K4 and K5 according to the following equations;

$$C2/C1 = (((1-T_{C2})/(1-T_{C1}))^{K3b} \cdot K4 + ((1-T_{C3})/(1-T_{C1})) \cdot K5 \quad (1b)$$

$$C3/C1 = (((1-T_{C3})/(1-T_{C1}))^{K3b} \cdot K4 + ((1-T_{C3})/(1-T_{C1})) \cdot K5 \quad (2b)$$

$$K4 + K5 = 1 \quad (3b)$$

cb) measuring a light transmissivity TM of the sample having an unknown concentration CM; and db) determining the unknown concentration CM according to the following equation:

$$CM + ((((1-TM)/(1-T_{C1}))^{K3b} \cdot K4 + ((1-TM)/(1-T_{C1})) \cdot K5) \cdot C1 \quad (4b).$$

4. The concentration measuring method according to claim 3, wherein a light transmissivity $TA = T_{C1}$, $T_{C2}$, $T_{C3}$ or TM of the first standard, the second standard, the third standard or the sample is determined by the steps of:

e) obtaining a first output D0 of a photodetector when no light enters the photodetector, and a second output D100 of the photodetector when light passing through a zero control containing zero percentage of the component enters the photodetector;

f) calculating a correction factor K1 based on the first output D0 and the second output D100 as $$K1 = 1/(D100 - D0) \quad (6)$$

g) obtaining an output DA of the photodetector when light passing through the first standard, the second standard, the third standard or the sample enters the photodetector, and determining the light transmissivity TA of the first standard, the second standard, the third standard or the sample as $$TA = (DA - D0) \cdot K1 \quad (8).$$

5. An apparatus for determining a concentration of a component in a sample comprising:

a) a sample cell for containing the sample;
b) a light source;
c) means for measuring a light transmissivity of the sample or standards in the sample;
d) means for calculating a correction factor K3 according to the following equations:

$$L_{C1} = \log((T_{C1} - K3)/(1-K3)) \quad (1)$$

$$L_{C2} = \log((T_{C2} - K3)/(1-K3)) \quad (2)$$

$$L_{C1}/L_{C2} = C1/C2 \quad (3)$$

where $T_{C1}$ AND $T_{C2}$ are light transmissivities of a first standard and a second standard respectively having known concentrations C1 and C2 of the component;

e) means for determining the concentration CM of the component in the sample according to either of the following equations:

$$CM = ((\log((TM - K3)/(1-K3))/L_{C1}) \cdot C1 \quad (4)$$

$$CM = ((\log((TM - K3)/(1-K3)/L_{C2}) \cdot C1 \quad (5)$$

where TM is a light transmissivity of the sample.

6. The concentration measuring apparatus according to claim 5, wherein the transmissivity measuring means comprises:

c1) a photodetector for measuring light passing through the sample cell;

c2) means for calculating a correction factor K1 according to the following equation $$K1 = 1/(D100 - D0) \quad (6)$$

where D0 is a first output of the photodetector when no light enters the photodetector, and D100 is a second output of the photodetector when light passing through a zero control containing zero percentage of the component enters the photodetector;

c3) means for determining a light transmissivity TA of the first standard, the second standard or the sample as $$TA = (DA - D0) \cdot K1 \quad (8)$$

where DA is an output of the photodetector when light passing through the first standard, the second standard or the sample enters the photodetector.

7. An apparatus for determining a concentration of a component in a sample comprising:

a) a sample cell for containing the sample;
b) a light source;
c) means for measuring a light transmissivity of the sample or standards in the sample cell;
d) means for calculating correction factors K3b, K4 and K5 according to the following equations:

$$C2/C1 = (((1-T_{C2})/(1-T_{C1}))^{K3b} \cdot K4 + ((1-T_{C2})/(1-T_{C1})) \cdot K5 \quad (1b)$$

$$C3/C1 = (((1-T_{C3})/(1-T_{C1}))^{K3b} \cdot K4 + ((1-T_{C3})/(1-T_{C1})) \cdot K5 \quad (2b)$$

$$K4 + K5 = 1 \quad (3b)$$

where $T_{C1}$, $T_{C2}$ and $T_{C3}$ are light transmissivities of a first standard, a second standard and a third standard respectively having known concentrations C1, C2 and C3 of the component;

e) means for determining the concentration CM of the component in the sample according to the following equation:

$$CM + ((((1-TM)/(1-T_{C1}))^{K3b} \cdot K4 + ((1-TM)/(1-T_{C1})) \cdot K5) \cdot C1 \quad (4b)$$

where TM is a light transmissivity of the sample.

8. The concentration measuring apparatus according to claim 7, wherein the transmissivity measuring means comprises:

c1) a photodetector for measuring light passing through the sample cell;

c2) means for calculating a correction factor K1 according to the following equation $$K1 = 1/(D100 - D0) \tag{6}$$

where D0 is a first output of the photodetector when no light enters the photodetector, and D100 is a second output of the photodetector when light passing through a zero control containing zero percentage of the component enters the photodetector;

c3) means for determining a light transmissivity TA of the first standard, the second standard, the third standard or the sample as $$TA = (DA - D0) \cdot K1 \tag{8}$$

where DA is an output of the photodetector when light passing through the first standard, the second standard, the third standard or the sample enters the photodetector.

* * * * *